(12) United States Patent
Johnson et al.

(10) Patent No.: US 7,479,399 B1
(45) Date of Patent: Jan. 20, 2009

(54) SYSTEM AND METHOD FOR PROVIDING AUTOMATED SAMPLE PREPARATION FOR PLAN VIEW TRANSMISSION ELECTRON MICROSCOPY

(75) Inventors: Mark Alan Johnson, Portland, ME (US); Larry W. Mayes, Lewiston, ME (US)

(73) Assignee: National Semiconductor Corporation, Santa Clara, CA (US)

( * ) Notice: Subject to any disclaimer, the term of this patent is extended or adjusted under 35 U.S.C. 154(b) by 0 days.

(21) Appl. No.: 11/804,896

(22) Filed: May 21, 2007

Related U.S. Application Data

(63) Continuation of application No. 10/903,367, filed on Jul. 30, 2004, now Pat. No. 7,250,318.

(51) Int. Cl.
*H01L 21/00* (2006.01)

(52) U.S. Cl. ............. 438/33; 438/68; 438/113; 438/118; 438/460; 438/464; 438/FOR. 386; 267/620; 267/E23.179

(58) Field of Classification Search ............. 438/33, 438/68, 113, 118, 460, 464, FOR. 386; 257/620, 257/E23.179
See application file for complete search history.

(56) References Cited

OTHER PUBLICATIONS

Wayne D. Kaplan et al., "Automatic TEM Sample Preparation", Proceedings from the 25th International Symposium for Testing and Failure Analysis, Nov. 14-18, 1999, Santa Clara, California, pp. 103-107.

Ron Anderson et al., "Combined Tripod Polishing and FIB Method for Preparing Semiconductor Plan View Specimens", Material Research Society Symposium Proceedings vol. 480, 1997, pp. 187-192.

*Primary Examiner*—Thanh V Pham

(57) ABSTRACT

A system and method is described for providing automated sample preparation for plan view transmission electron microscopy. A sample wafer is microcleaved from a semiconductor wafer and mounted on a first support stub. Then the sample wafer is cut with an automated diamond sawing tool to expose a cross sectional view of the sample wafer. The sample wafer is removed from the first support stub and rotated to orient the sample wafer for plan view imaging. The rotated sample wafer is then remounted on a second support stub and cut with the automated diamond sawing tool to expose a plan view surface of the rotated sample wafer. The remounted sample wafer is subsequently prepared for focused ion beam (FIB) milling and plan view transmission electron microscopy imaging.

18 Claims, 9 Drawing Sheets

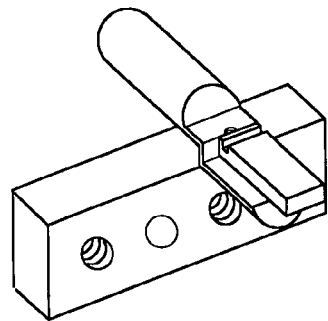
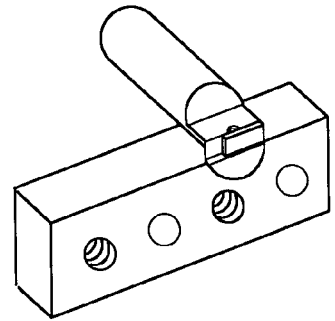
FIG. 5   FIG. 6
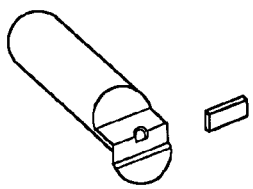
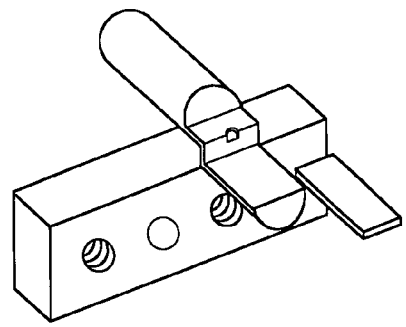
FIG. 7   FIG. 8
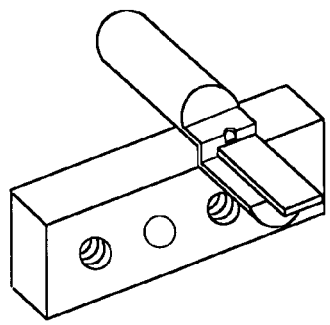
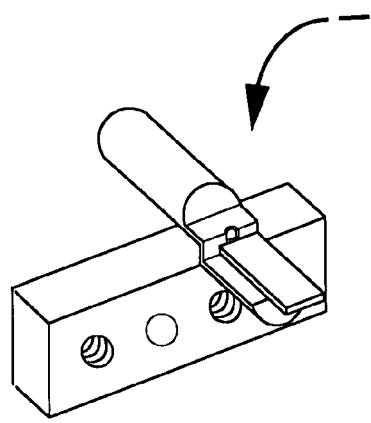
FIG. 9   FIG. 10

SYSTEM AND METHOD FOR PROVIDING AUTOMATED SAMPLE PREPARATION FOR PLAN VIEW TRANSMISSION ELECTRON MICROSCOPY

This application is a continuation of prior U.S. patent application Ser. No. 10/903,367 filed on Jul. 30, 2004, now U.S. Pat. No. 7,250,318.

TECHNICAL FIELD OF THE INVENTION

The present invention is generally directed to manufacturing technology for semiconductor circuits and, in particular, to a system and method for providing automated sample preparation for plan view transmission electron microscopy.

BACKGROUND OF THE INVENTION

Increasingly smaller geometries and feature sizes of semiconductor devices have made transmission electron microscopy (TEM) an increasing important characterization technique for semiconductor product development and failure analysis. Resolution of less than fifteen hundredths of a nanometer (0.15 nm) allows TEM to provide structural information down to the atomic level. TEM can also be used in conjunction with X-ray or electron energy loss spectrometers to provide information on chemical composition at sub-nanometer length scales. See, for example, D. B. Williams and C. B. Carter, *Transmission Electron Microscopy. A Textbook for Materials Science*, Plenum Press, New York, 1996.

The chief difficulty associated with TEM has traditionally been the preparation of samples. D. K. Schroeder, *Semiconductor Material and Device Characterization*, Second Edition, John Wiley & Sons, New York, 1998. Samples for TEM analysis must be less than two hundred fifty nanometers (250 nm) thick in order to achieve good image quality. The increasing demand for TEM analysis in the semiconductor industry has placed a high priority on reducing the time and labor required to prepare a TEM sample.

One of the earliest techniques for preparing TEM samples from semiconductor materials is mechanical lapping-polishing. S. J. Klepieis, J. P. Benedict and R. M. Anderson, Specimen Preparation for Transmission Electron Microscopy of Materials, Materials Research Society Symposium Proceedings 115, p. 179, Materials Research Society, Pittsburgh, Pa., 1988. In mechanical lapping-polishing a small piece of semiconductor wafer containing the sample site is mounted on a tripod polisher. The tripod polisher holds the wafer against a rotating abrasive disc. A series of progressively finer abrasives are used with water rinse to reduce the sample to electron transparency. The mechanical lapping-polishing technique typically takes four to five hours to complete. The mechanical lapping-polishing technique can be used to prepare both plan-view samples and cross-sectional samples of a semiconductor wafer. FIG. 1 illustrates a schematic view of one half of an exemplary prior art semiconductor wafer 100 showing an exemplary portion of a plan-view 110 of the wafer 100 and an exemplary portion of a cross-sectional view 120 of the wafer 100.

The prior art mechanical lapping-polishing technique can also be performed automatically. Sagitta Corporation has developed an automatic tool for mechanically lapping-polishing both TEM samples and Scanning Electron Microscopy (SEM) samples. G. A. Schechter, L. Adams, and I. Ward, SEM/TEM Sample Preparation, Solid State Technology, pp. S1-S8, September, 2000. The Sagitta automatic tool speeds up the polishing process by removing all of the manual inspections required to check the progress during the tripod polishing process in order to avoid polishing away the site of interest.

The past fifteen (15) years have seen a trend toward the increased use of focused ion beam (FIB) milling tools for the preparation of TEM samples. Site-specific TEM samples can be prepared faster and easier using an FIB milling tool than by polishing. FIB preparation is typically done with a dual beam instrument employing an ion column for milling and an SEM column for imaging. The ion column uses a beam of gallium ions to remove unwanted material and expose a fresh surface passing through the region of interest. Progress is monitored with secondary electron images taking throughout the milling process.

Several techniques have been developed to make FIB-milled cross-sectional samples compatible with the standard three millimeter (3 mm) diameter TEM sample holder. One such technique is to use tripod polishing for the initial sizing of the sample. R. Anderson and S. J. Klepeis, Specimen Preparation for Transmission Electron Microscopy of Material IV, Materials Research Society Symposium Proceedings V.480, p. 187, Materials Research Society, Pittsburgh, Pa., 1997. In this approach the sample is polished to a thickness of approximately thirty microns (30 µm) and then mounted on a modified copper support grid that is compatible with milling in the FIB and with the TEM sample holder. Prior to use, the sample holder grid is modified by manually cutting away one parallel side to allow access for the ion beam during the milling process. Finally, the sample is transferred into an FIB instrument for ultimate thinning to electron transparency. This approach can be used for both plan-view samples and cross-section samples.

Another approach for making FIB preparation compatible with TEM sample holders is a technique known as "µ-sampling". This approach involves the transfer of FIB-milled TEM samples directly from a semiconductor chip or wafer onto a copper support grid using micro-manipulators. See, for example, M. H. F. Overwijk, F. C. van den Heuvel, and C. W. T. Bulle-Lieuwma, Journal of Vacuum Science and Technology, B11, p. 2021 (1993); L. A. Giannuzzi, J. L. Drown, S. R. Brown, R. B. Irwin, and F. A. Steive, Materials Research Society Symposium Proceedings, Volume 480 on Specimen Preparation for Transmission Electron Microscopy of Materials IV, p. 19, American Institute of Physics, New York, 1997; L. A. Giannuzzi, J. L. Drown, S. R. Brown, R. B. Irwin, and F. A. Steive, Micros. Res. Tech. 41, p. 285, 1998; and T. Onishi, H. Koike, T. Ishitani, S. Tomimatsu, K. Umemura, and T. Kamino, A New Focused-Ion Beam Microsampling Technique for TEM Observation of Site-Specific Areas, Proceedings of the Twenty Fifth International Symposium for Testing and Failure Analysis, pp. 449-453, 1999.

The "µ-sampling" technique avoids many of the "pre-preparation" steps such as wafer cleaving, sawing, and tripod polishing, but it does so at the expense of increased time spent on the FIB preparation of the sample. The high cost and heavy usage commonly associated with FIB instruments make any increase in instrument time for sample preparation a potential factor in bottlenecking laboratory output.

A third approach for making FIB preparation compatible with TEM sample holders is a technique developed by the Semiconductor Engineering Laboratories Corporation (SELA) The technique will be referred to as the "SELA process". A more detailed discussion of the SELA process is set forth in W. D. Kaplan, R. Oviedo, K. Kisslinger, E. M. Raz and C. Smith, Automatic TEM Sample Preparation, Proceedings of the Twenty Fifth International Symposium for Testing and Failure Analysis, pp. 103-107, 1999; and in R. Reyes, F.

Shaapur, D. Griffiths, A. C. Diebold, B. Foran, and E. Raz, Automated SEM and TEM Sample Preparation Applied to Copper/Low K Materials, AIP Conference Proceedings, pp. 580-585, 2001.

The SELA process automates the initial wafer cleaving and thinning steps for cross-sectional semiconductor sample preparation. The SELA process proceeds in two steps. In the first step an automated microcleaver is used to cut the samples. The automated microcleaver has an accuracy of one fourth of a micron (0.25 μm). In the second step the samples that are output from the automated microcleaver are then provided to a rotary diamond saw (referred to as a "TEMpro™" unit). An earlier version of the TEMpro™ unit is referred to as a "TEMstation™" unit. "TEMpro™" and "TEMstation™" are trademarks of the Semiconductor Engineering Laboratories Corporation (SELA).

The two SELA tools (i.e., the automated microcleaver and the rotary diamond saw ("TEMpro™")) automatically mount the sample on a TEM-compatible copper support grid and use a series of diamond saws to reduce the sample to an approximate thickness of thirty microns (30 μm). The result is a TEM-compatible, site-specific, cross-section sample that is ready for FIB milling. By consistently and quickly achieving a sample thickness of thirty microns (30 μm) the SELA process is aimed at a high throughput of TEM samples by eliminating the steps of tripod polishing and by minimizing FIB instrument time.

The prior art SELA process provides automated sample preparation for obtaining cross-sectional views of transmission electron microscopy. However, there is no similar method for preparing samples for plan view transmission electron microscopy.

There is therefore a need in the art for a system and method for providing automated sample preparation for plan view transmission electron microscopy. There is also a need in the art for a system and method that automatically prepares plan view transmission electron microscopy samples in manner that is not labor intensive.

SUMMARY OF THE INVENTION

To address the above-discussed deficiencies of the prior art, it is a primary object of the present invention to provide a system and method for providing automated sample preparation for plan view transmission electron microscopy (TEM).

In one advantageous embodiment of the method of the invention a sample wafer is microcleaved from a semiconductor wafer. The sample wafer is then mounted on a first copper support stub. Then the sample wafer is cut with an automated diamond sawing tool to expose a cross sectional view of the sample wafer. The sample wafer is then removed from the first copper support stub and rotated to orient the sample wafer for plan view imaging. The sample wafer is rotated ninety degrees (90°) to orient the sample wafer for plan view TEM imaging.

The rotated sample wafer is then remounted on a second copper support stub and returned to the automated diamond sawing tool. The automated diamond sawing tool then cuts the rotated sample wafer to expose a plan view surface of the rotated sample wafer. The remounted sample wafer is then prepared for subsequent focused ion beam (FIB) milling and subsequent plan view TEM imaging.

The processing time required for performing the method of the present invention is approximately forty (40) minutes. This amount of time is approximately twice as long as the processing time required for the standard SELA process for cross-sectional TEM samples. The processing time required by the present invention represents a substantial time saving when compared to the processing time required for the prior art methods of preparing plan view samples using tripod polishing. The processing time required by the present invention also represents a substantial time saving when compared to the processing time required for the prior art method of polishing plan view samples in preparation for FIB milling.

The automated nature of the method of the present invention also allows laboratory personnel to work on other tasks while the SELA tools are operating. The possibility of the laboratory personnel being able to "multitask" in this manner does not exist in the case of the prior art processes (e.g., mechanical lapping-polishing).

It is an object of the present invention to provide a system and method for providing automated sample preparation for plan view TEM imaging.

It is also an object of the present invention to provide a system and method for rotating a sample wafer to orient the sample wafer for plan view TEM imaging.

It is yet another object of the present invention to provide a system and method for remounting a rotated sample wafer on a spacer wafer on a second copper support stub to prepare the sample wafer for plan view TEM imaging.

It is still another object of the present invention to provide a system and method for the automated preparation of sample wafers for plan view TEM imaging to allow laboratory personnel to be free to work on other tasks while the sample wafers of the present invention are automatically being prepared.

It is another object of the present invention to provide sample wafers that are rotated and remounted on a copper support stub in an orientation that facilitates plan view TEM imaging of the sample wafers.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description of the Invention below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior uses, as well as future uses, of such defined words and phrases.

BRIEF DESCRIPTION OF THE DRAWINGS

For a more complete understanding of the present invention and its advantages, reference is now made to the following description taken in conjunction with the accompanying drawings, in which like reference numerals represent like parts:

FIG. 5 illustrates the result of a first saw step performed on the input sample wafer shown in FIG. 4;

FIG. 6 illustrates the result of a second saw step performed on the input sample wafer shown in FIG. 5;

FIG. 7 illustrates the result of removing the input sample wafer from the copper support stub shown in FIG. 6;

FIG. 8 illustrates a spacer wafer and a new copper support stub to which the spacer wafer is to be glued;

FIG. 9 illustrates the result of gluing the spacer wafer to the new copper support stub shown in FIG. 8;

FIG. 10 illustrates the transfer of the sample wafer shown in FIG. 7 to the spacer wafer shown in FIG. 9;

DETAILED DESCRIPTION OF THE INVENTION

Figure 1:
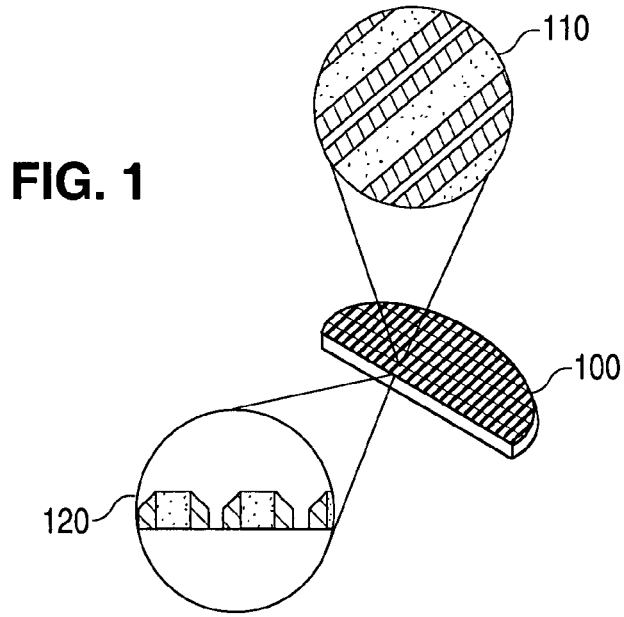
FIG. 1 illustrates a schematic view of one half of an exemplary prior art semiconductor wafer showing an exemplary portion of a plan-view of the wafer and an exemplary portion of a cross-sectional view of the wafer.

FIGS. 2 through 24, discussed below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device for preparing plan-view TEM samples.

To simplify the drawings the reference numerals from previous drawings may sometimes not be repeated for structures that have already been identified.

The automated plan-view TEM sample preparation method of the present invention comprises a four stage process. The four stages are: (1) microcleaving process, (2) initial sawing process, (3) remounting process, and (4) final sawing process. The resulting TEM sample comprises a thirty micron (30 µm) thick section of silicon wafer glued onto a TEM-compatible support grid, with circuitry containing the site of interest exposed on the top surface. The sample is ready for plan-view FIB milling and subsequent TEM imaging. The figures described below comprise a series of diagrams that illustrate the operations that make up the four stages of the method of the present invention.

MICROCLEAVING PROCESS. The first stage in the method of the present invention comprises a microcleaving process. The microcleaving process is accomplished using either the SELA MC500 automated microcleaver or its predecessor the SELA MC200 automated microcleaver (not shown in the figures). The automated microcleaver uses point-and-click operating software and digital imaging to achieve very precise and accurate cleaving of the area of interest of a semiconductor wafer. The accuracy of the cleaving process is plus or minus one fourth of a micron (+/−0.25 µm) For general background information on microcleaving refer to C. Smith, Microcleaving, European Semiconductor, January 1995.

Input to the SELA MC200 automated microcleaver is a section of semiconductor wafer that is eleven millimeters (11 mm) to thirteen millimeters (13 mm) wide and forty millimeters (40 mm) to eighty millimeters (80 mm) long. The site of interest is typically located in the middle third of the wafer section and not more than one millimeter (1 mm) in from an alignment edge. The user then selects a location for the cleave, typically three microns (3 µm) to five microns (5 µm) from the site of interest. The automated microcleaver then proceeds to mark the selected location with a diamond scribe and then cleaves the wafer at the selected location. The new cleave then becomes the prime edge for the diamond saw TEMpro™ tool (or the diamond saw TEMstation™ tool). The microcleaving process usually takes fewer than fifteen minutes to perform.

INITIAL SAWING PROCESS. The second stage in the method of the present invention comprises an initial sawing process. The initial sawing process (and the subsequent remounting step and the final sawing process of the method) utilizes the SELA TEMpro™ diamond sawing tool (or its predecessor the SELA TEMstation™ diamond sawing tool). The SELA diamond sawing tools were developed as high throughput automated devices for preparing cross-sectional TEM samples from semiconductor wafers. The SELA diamond sawing tools take microcleaved samples from the MC500 automated microcleaver (or the MC200 microcleaver) as input and employ a series of rotary diamond saws to reduce the sample to a size suitable for rapid FIB milling. As part of this process the sample is mounted onto a copper disc compatible with most TEM sample holders. The process time for the cross-sectional samples is typically fifteen to twenty minutes. The process time for the plan-view samples in accordance with the principles of the present invention takes approximately twice as long (i.e., thirty to forty minutes) as the process time for the cross-sectional samples.

Figure 2:
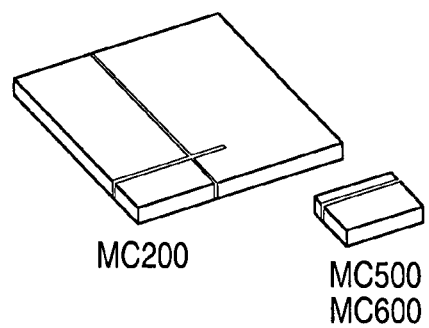
FIG. 2 illustrates an exemplary input sample wafer in the shape of a rectangle cut from a microcleaver sample.
Figures 3, 4:
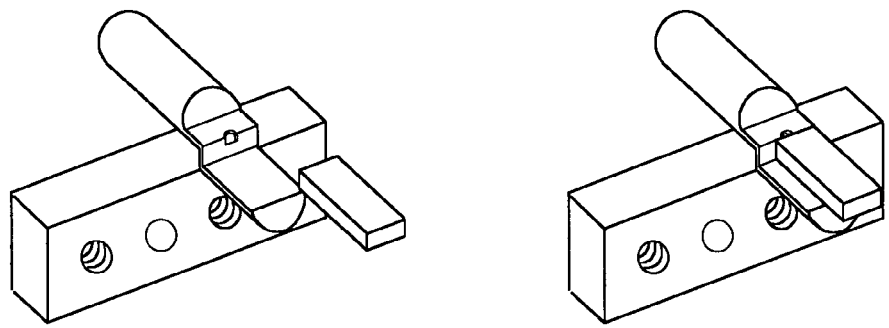
FIG. 3 illustrates the input sample wafer shown in FIG. 2 before it is glued to a copper support stub.
FIG. 4 illustrates the input sample wafer shown in FIG. 3 after it is glued to the copper support stub.

In the first step of the initial sawing process the TEMpro™ diamond saw makes a presaw cut. The presaw cut serves to remove the excess material that is required for the microcleaver. As shown in FIG. 2, the presaw cut cuts a one and one half millimeter (1.5 mm) by three millimeter (3 mm) rectangle 200 from the corner of the microcleaver sample 210. The site of interest is situated along the prime edge and forms one of the one and one half millimeter (1.5 mm) sides of the rectangle 200. The output from the presaw cut is automatically glued to a copper support stub 300, as shown in FIG. 3 and in FIG. 4. The copper support stub 300 is mounted on a stub holder fixture 310. The copper support stub 300 supports the sample 200 during subsequent wafer sawing operations and ultimately helps to make output from the TEMpro™ diamond saw compatible with standard three millimeter (3 mm) diameter TEM sample holders.

Although the support stub 300 is stated to be a copper support stub 300, it is noted that the invention is not limited to the use of copper material for the support stub. Any other suitable material may be used in place of copper in the manufacture of a support stub.

The next step in the initial sawing process is referred to as the first saw step. FIG. 5 illustrates the first saw step. For cross-sectional samples the first saw step establishes the thirty micron (30 µm) width of the wafer that remains as the completed TEMpro™ sample. For preparation of the plan-view samples, the first saw width is increased to the maximum permissible width in the TEMpro™ diamond saw. The maximum permissible width in the TEMpro™, diamond saw is presently approximately ninety microns (90 µm). The software routine in the TEMpro™ diamond saw that controls the maximum permissible width may be modified to increase the maximum permissible width to more than ninety microns (90 µm) in order to facilitate the preparation of plan-view TEM samples.

The first saw cut is intentionally made shallow in order to preserve the accuracy and precision of the diamond blade used to cut the wafer. The depth of the first saw cut is approximately one hundred sixty microns (160 µm) and is not intended to cut the full thickness of the sample wafer 200.

The next step in the initial sawing process is referred to as the second saw step. Another diamond blade that is referred to as the second saw is used to complete the cut through the full thickness of the wafer 200 and also through the copper support stub 300. The diamond blade of the second saw is coarser than the diamond blade of the first saw. The coarser diamond blade of the second saw is sufficiently accurate for cutting through the rest of the wafer 200 and through the copper support stub 300. The result of the second saw step is shown in FIG. 6.

REMOUNTING PROCESS. The most important process modifications for the preparation of plan-view samples occur after the initial saw process has been completed. These modifications are required to re-position the sample wafer 200 relative to the TEMpro™ copper support stub 300 so that the completed sample 200 has its circuitry oriented correctly for plan-view imaging in TEM. The third stage in the method of the present invention comprises a remounting process. The software routine used to operate the first saw cut and the second saw cut is terminated and the sample wafer 200 is unloaded from the TEMpro™ diamond saw.

The copper support stub 300 with the sample wafer 200 attached to it is then removed from the stub holder fixture 310 and placed into a solution of glue removal solvent. After soaking for about twenty five minutes in the glue removal solvent (e.g., Loctite X-NMS Cleanup Solvent) the sample wafer 200 is completely freed from the copper support stub 300. This result is shown in FIG. 7. All traces of the glue removal solvent are removed by soaking the sample wafer 200 for a few minutes in acetone and then in isopropyl alcohol. The sample wafer 200 is then allowed to air dry.

Now the sample wafer 200 is ready to be glued to a fresh copper support stub 800 in the proper orientation for plan-view imaging. The new copper support stub 800 is mounted on the stub holder fixture 310. For plan-view imaging the sample wafer 200 is rotated ninety degrees (90°) so that the circuitry is on one side of the sample wafer 200, instead of being edge-on as in the case of a cross-sectional sample wafer. Because the maximum width of the first saw cut is one hundred microns (100 µm), the rotated sample wafer 200 is not the standard wafer thickness required for the TEMpro™ diamond saw.

In order to compensate for the difference in width, a spacer wafer 810 is prepared from a one hundred millimeter (100 mm) diameter wafer with a one-zero-zero (100) lattice orientation. The spacer wafer 810 is approximately four hundred eighty microns (480 µm) thick, so that the combined thickness of the spacer wafer 810 and the sample wafer 200 together is approximately five hundred seventy microns (570 µm). This thickness is a good match for the height of the ledge that holds the sample wafer 200 in the copper support stub 800. The use of a spacer wafer 810 can be dispensed with if a modification is made to the TEMpro™ diamond saw to permit thicker first saw cuts. The spacer wafer 810 is subjected to the presaw cut in the TEMpro™ diamond saw. The spacer wafer 810 is removed from the instrument after it has been glued to a new copper support stub 800, as shown in FIG. 8 and in FIG. 9.

Figure 11:
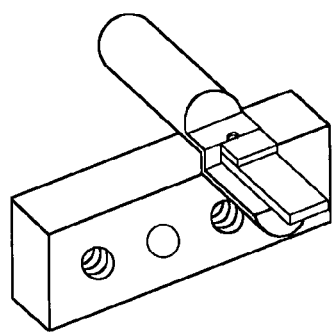
FIG. 11 illustrates the result of gluing the sample wafer shown in FIG. 10 to the spacer wafer shown in FIG. 10.
Figure 12:
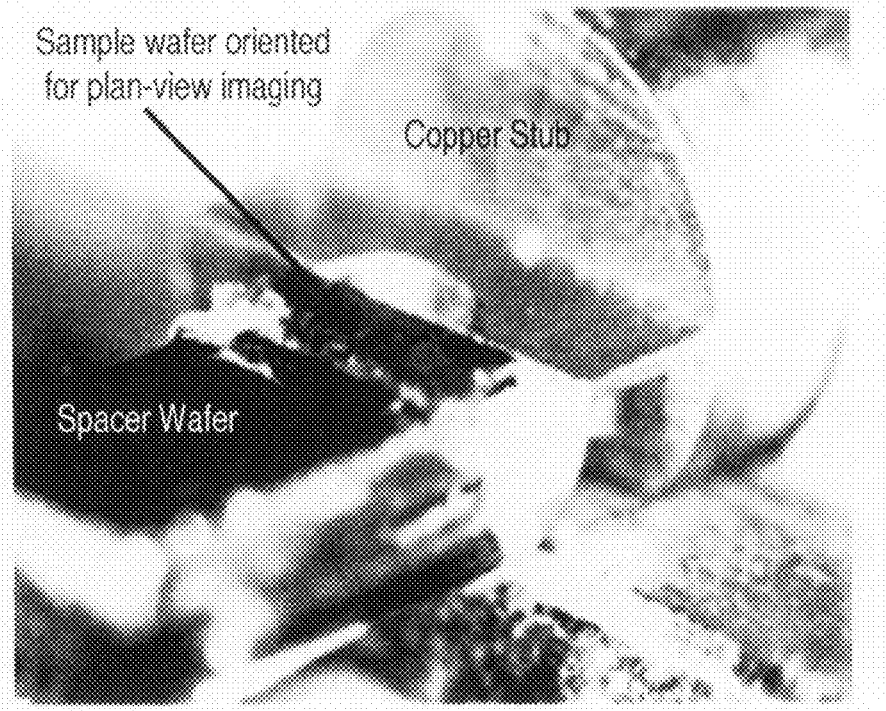
FIG. 12 illustrates a three quarter side view of the sample wafer after the sample wafer has been glued to the spacer wafer and remounted on a copper support stub.
Figure 13:
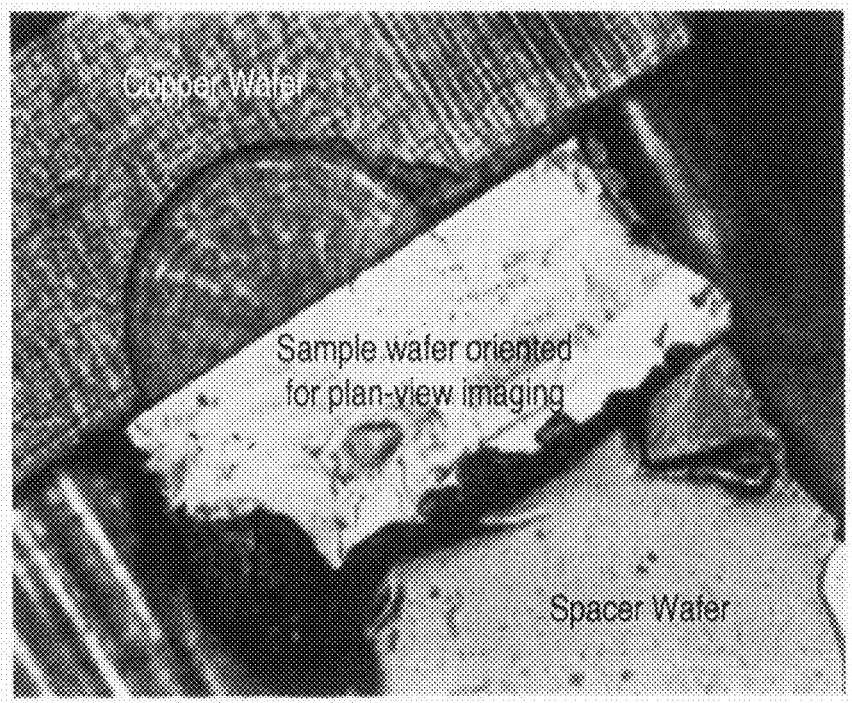
FIG. 13 illustrates a top down view of the sample wafer after the sample wafer has been glued to the spacer wafer and remounted on a copper support stub.

The remounting process is completed by transferring the sample wafer 200 to the spacer wafer 810 as shown in FIG. 10 and then gluing the sample wafer 200 to the top of the spacer wafer 810 as shown in FIG. 11. Proper orientation of the sample wafer 200 during this gluing step is critical to insure that the target site is correctly positioned for plan-view imaging. The sample wafer 200 is oriented with its microcleaved surface facing upwards and its circuitry pushed up against the vertical wall of the copper support stub 800. This positions the target site inside of the imaging window in the copper support stub 800. FIG. 12 shows a three quarter side view of the sample wafer 200 after the sample wafer 200 has been glued to the spacer wafer 810 and remounted on a copper support stub 800. FIG. 13 shows a top down view of the sample wafer 200 after the sample wafer 200 has been glued to the spacer wafer 810 and remounted on a copper support stub 800.

Transfer of the sample wafer 200 onto the spacer wafer 810 is done under a stereomicroscope using a vacuum wand with a fine-tipped needle attachment. The needle bevel is blunted for personal safety and to facilitate handling the sample. A twenty millimeter (20 mm) long needle, gauge twenty three (23) to twenty six (26), is ideal for this and is small enough that it does not swallow up the sample wafer 200. A special fixture (not shown) may be used to hold the copper support stub 800, the vacuum wand, and the plan-view sample 200 during the remounting process in order to make the remounting process easier and faster.

Figure 14:
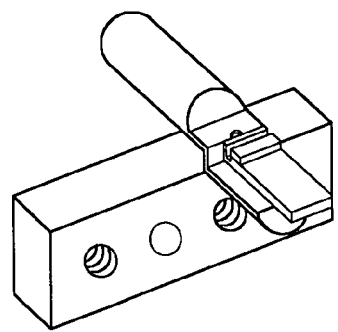
FIG. 14 illustrates the result of applying a plan-view first saw cut to the sample wafer shown in FIG. 11.

FINAL SAWING PROCESS. The fourth stage in the method of the present invention comprises a final sawing process. The method of plan-view sample preparation is completed by returning the remounted sample wafer 200 to the TEMpro™ diamond saw. A software routine that is known as "Partial Process" is selected in order to avoid making a presaw cut. So the TEMpro™ diamond saw begins with a plan-view first saw cut. In this case the standard thirty micron (30 µm) cut is selected for the plan-view first saw width, as shown in FIG. 14.

Figure 15:
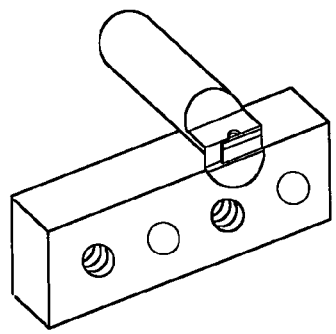
FIG. 15 illustrates the result of applying a plan-view second saw cut to the sample wafer shown in FIG. 14.
Figure 16:
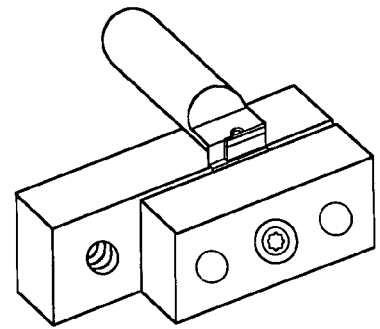
FIG. 16 illustrates the result of clamping a focused ion beam (FIB) clamp to the sample wafer and copper support stub shown in FIG. 15.

The plan-view first saw cut is followed by a plan-view second saw cut to remove excess material from the sample wafer 200 and the spacer wafer 810 and the copper support stub 800, as shown in FIG. 15. After the plan-view second saw cut has been completed the sample wafer 200 (and the spacer wafer 810) and the stub holder fixture 310 are removed from the TEMpro™ diamond saw and an FIB clamp 1600 is attached to the sample wafer. The FIB clamp 1600 helps to hold the sample 200 in place during a plan-view third saw cut and also during subsequent FIB milling, as shown in FIG. 16.

Figure 17:
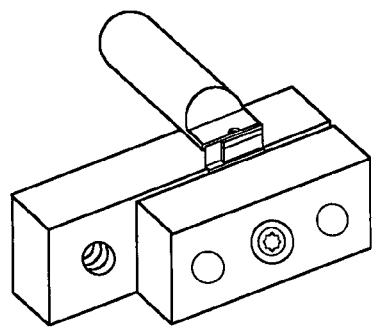
FIG. 17 illustrates the sample wafer and copper support stub and FIB clamp as shown in FIG. 16 ready to receive a plan-view third saw cut to remove the copper support stub.
Figure 18:
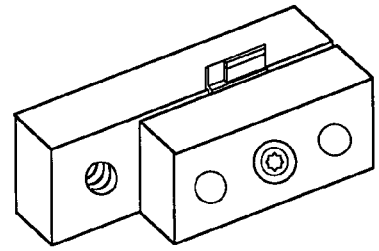
FIG. 18 illustrates the result of applying a plan-view third saw cut to the sample wafer and copper support stub and FIB clamp shown in FIG. 17.

Finally, the sample wafer 200, the stub holder fixture 310, and the FIB clamp 1600 are returned to the TEMpro™ diamond saw for a plan-view third saw cut, as shown in FIG. 17. This is the last step in the final sawing process stage of the method and serves to completely sever the completed sample wafer 200 from the copper support stub 800. After the plan-view third saw cut the plan-view sample wafer 200 is ready for FIB milling and subsequent TEM imaging, as shown in FIG. 18.

Figure 19:
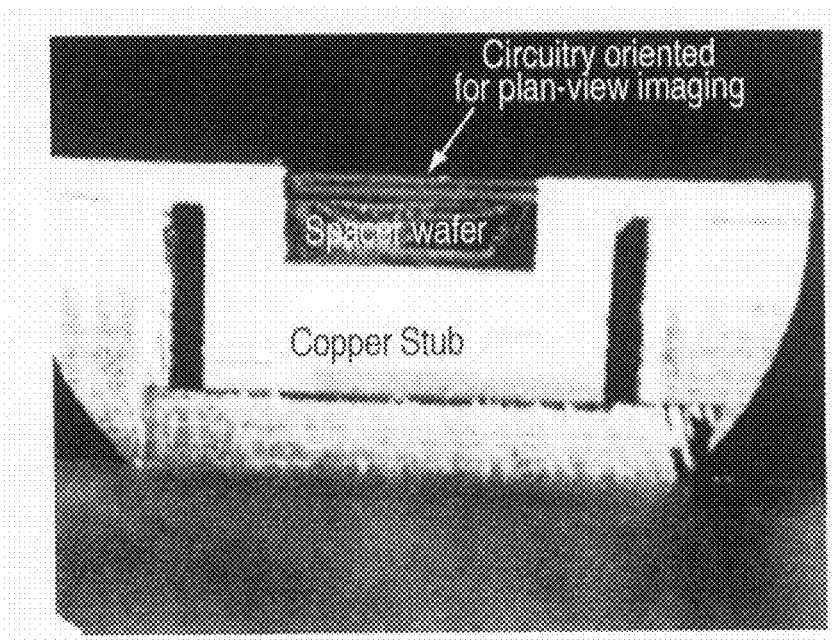
FIG. 19 illustrates an optical image of a first side of a completed TEM sample with circuitry correctly oriented for plan-view imaging.
Figure 20:
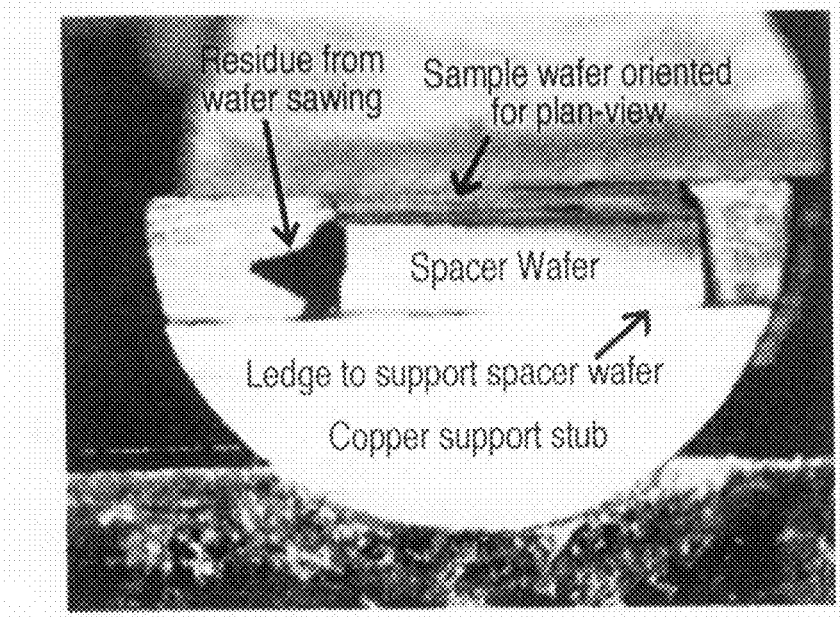
FIG. 20 illustrates an optical image of a second side of the completed TEM sample shown in FIG. 19.

The stages of the method of the present invention described above permit the automated SELA process to be used for the automated preparation of site-specific plan-view TEM samples for semiconductor applications. A TEM sample that is output from the method of the present invention is ready for plan-view FIB milling and is compatible with standard three millimeter (3 mm) TEM sample holders. FIG. 19 shows an optical image of a first side of a completed TEM sample with circuitry correctly oriented for plan-view imaging. FIG. 20 shows an optical image of a second side of the completed TEM sample shown in FIG. 19.

The processing time required for performing the method of the present invention is approximately forty (40) minutes. This amount of time is approximately twice as long as the processing time required for the standard SELA process for cross-sectional TEM samples. The processing time required by the present invention represents a substantial time saving when compared to the processing time required for the prior art methods of preparing plan-view samples using tripod polishing. The processing time required by the present invention also represents a substantial time saving when compared to the processing time required for the prior art method of polishing plan-view samples in preparation for FIB milling.

The automated nature of the method of the present invention also allows laboratory personnel to work on other tasks while the SELA tools are operating. The possibility of the laboratory personnel being able to "multitask" in this manner does not exist in the case of the prior art processes (e.g., mechanical lapping-polishing).

Figure 21:
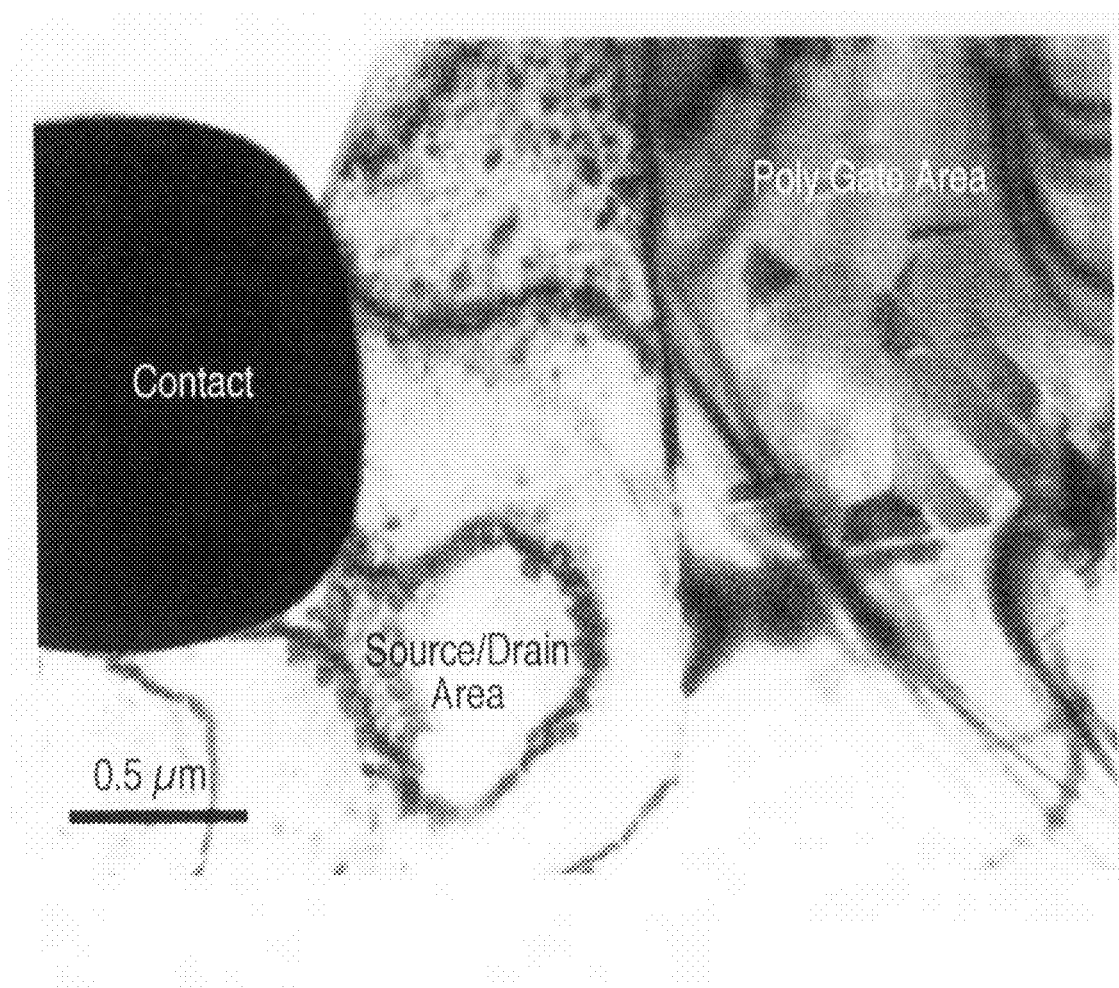
FIG. 21 illustrates an exemplary TEM image of an FIB-milled plan-view TEM sample manufactured in accordance with the method of the present invention.

FIG. 21 illustrates an exemplary TEM image of an FIB-milled plan-view TEM sample manufactured in accordance with the method of the present invention. FIG. 21 shows a poly gate area and a source/drain area with silicon dislocation loop defects.

Figure 22:
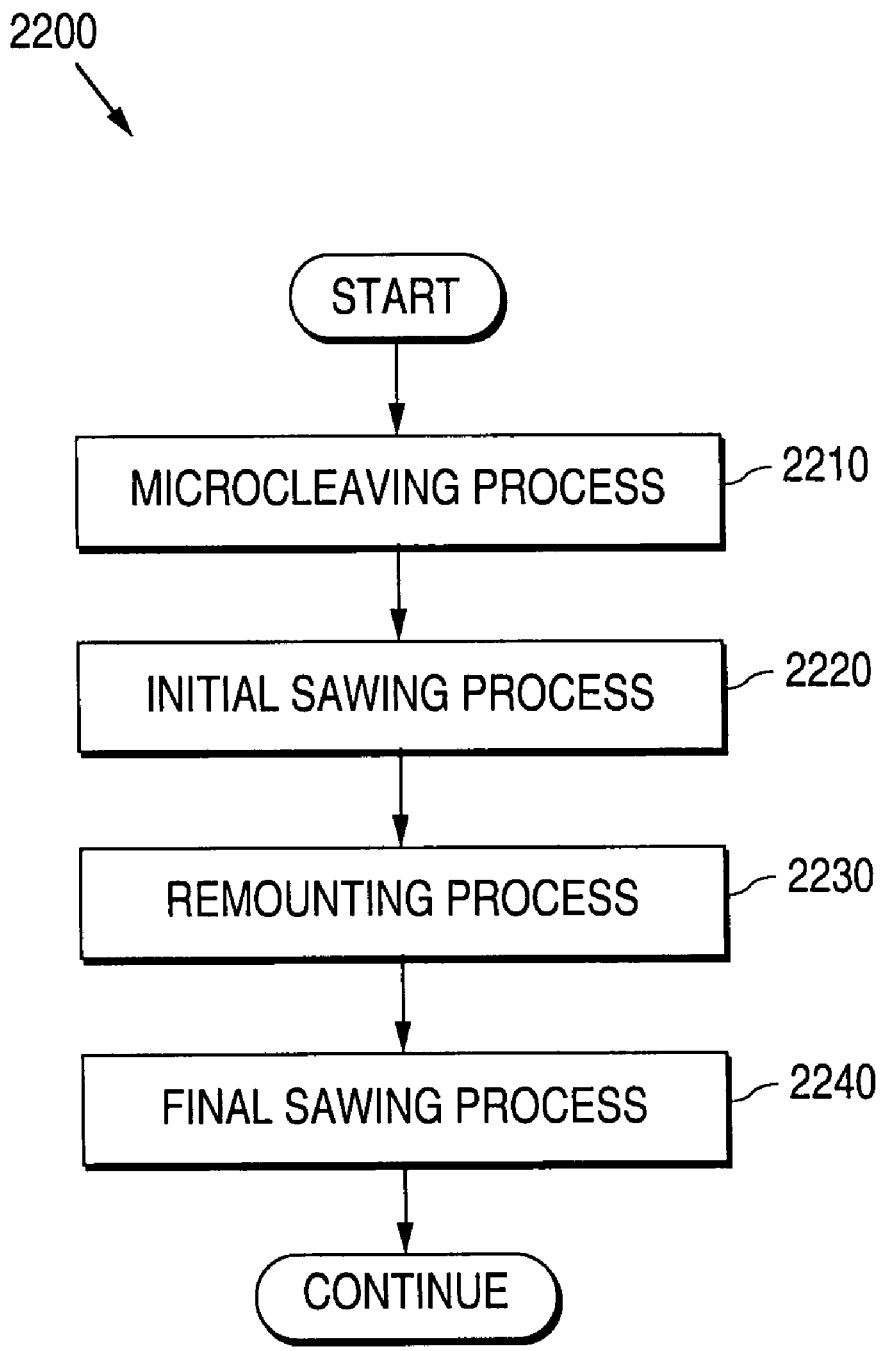
FIG. 22 illustrates a flow chart showing the steps of an advantageous embodiment of the method of the present invention.

FIG. 22 illustrates a flow chart 2200 showing the steps of an advantageous embodiment of the method of the present invention. In the first step of the method a microcleaving process is performed to accurately cleave an area of interest in a semiconductor wafer to create a sample wafer (step 2210). Then an initial sawing process is performed to prepare the sample wafer (step 2220). Then a remounting process remounts the sample wafer on a support stub with the sample wafer oriented for plan-view imaging (step 2230). Then a final sawing process is applied to the remounted sample wafer to prepare the remounted sample wafer for FIB milling and subsequent plan-view TEM imaging (step 2240).

Figure 23:
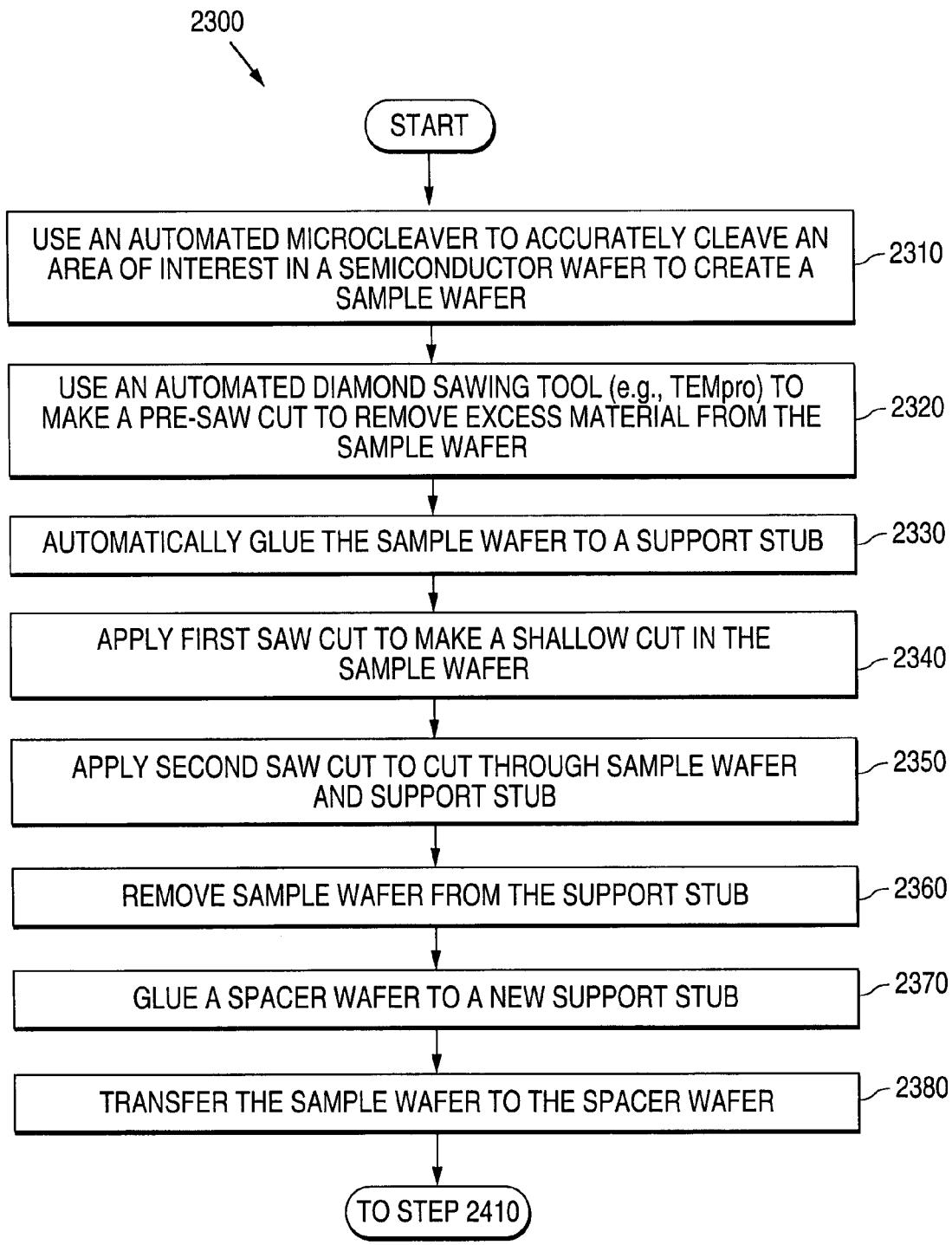
FIG. 23 illustrates a flow chart showing a more detailed version of the steps of a first portion of the method of the present invention shown in FIG. 22.

FIG. 23 illustrates a flow chart 2300 showing a more detailed version of the steps of a first portion of the method of the present invention shown in FIG. 22. In the first step of the method an automated microcleaver is used to accurately cleave an area of interest in a semiconductor wafer to create a sample wafer (step 2310). Then an automated diamond saw (e.g., a SELA TEMpro™ automated diamond saw) to make a pre-saw cut to remove excess material from the sample wafer (step 2320). Then the sample wafer is automatically glued to a support stub (e.g., a copper support stub) (step 2330).

Then a first saw cut is applied to the sample wafer to make a shallow cut in the sample wafer (step 2340). Then a second saw cut is applied to the sample wafer to cut through the sample wafer and the support stub (step 2350). Then the sample wafer is removed from the support stub (step 2360). Then a spacer wafer is glued to a new support stub (step 2370). The sample wafer is then transferred to the spacer wafer (step 2380). Control of the method then passes to step 2410 of FIG. 24.

Figure 24:
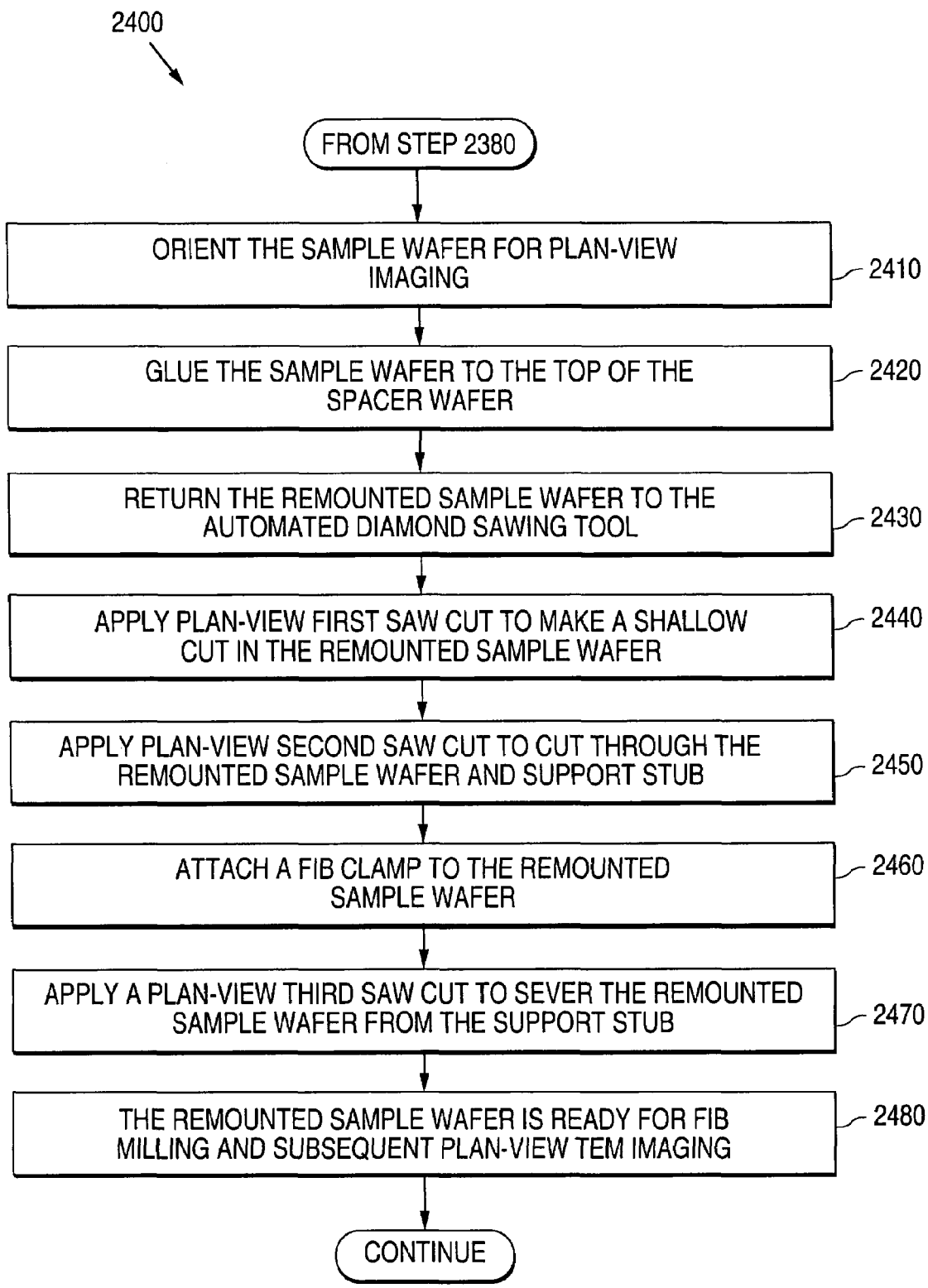
FIG. 24 illustrates a flow chart showing a more detailed version of the steps of a second portion of the method of the present invention shown in FIG. 22.

FIG. 24 illustrates a flow chart 2400 showing a more detailed version of the steps of a second portion of the method of the present invention shown in FIG. 22. Control of the method passes to the first step of the method in FIG. 24 from step 2380 of FIG. 23. First the sample wafer is oriented for plan-view imaging (step 2410). As previously described, the sample wafer is rotated ninety degrees (90°) so that the circuitry on the sample wafer is aligned properly for plan-view imaging. Then the sample wafer is glued to the top of the spacer wafer (step 2420).

Then the remounted sample wafer is returned to the automated diamond sawing tool (step 2430). The sawing tool is then used to apply a plan-view first saw cut to the remounted sample wafer to make a shallow cut in the remounted sample wafer (step 2440). Then the sawing tool is used to apply a plan-view second saw cut to cut through the remounted sample wafer and support stub (step 2450).

Then an FIB clamp is attached to the remounted sample wafer (step 2460). Then the sawing tool is used to apply a plan-view third saw cut to the remounted sample wafer to sever the remounted sample wafer from the support stub (step 2470). Then the remounted sample wafer is ready for FIB milling and subsequent plan-view TEM imaging (step 2480).

Although the present invention has been described with an exemplary embodiment, various changes and modifications may be suggested to one skilled in the art. It is intended that the present invention encompass such changes and modifications as fall within the scope of the appended claims.

What is claimed is:

1. A method for preparing a sample wafer for plan view transmission electron microscopy, the method comprising:
    microcleaving a sample wafer from a semiconductor wafer;
    cutting the sample wafer to expose a cross sectional view surface of a first remaining portion of the sample wafer;
    mounting a spacer to a support stub, and mounting the first remaining portion to the spacer in an orientation for plan view imaging; and cutting the first remaining portion to expose a plan view surface of a second remaining portion of the sample wafer.

2. The method of claim 1, wherein cutting the sample wafer comprises mounting the sample wafer on a first support stub.

3. The method of claim 2, wherein mounting the first remaining portion comprises:

removing the first remaining portion from the first support.

4. The method of claim 3, further comprising:

clamping a focused ion beam (FIB) clamp to a stub holder fixture that supports the second support stub; and cutting the second remaining portion of the sample wafer from the second support stub.

5. The method of claim 3, wherein mounting the first remaining portion on a second support stub comprises rotating the first remaining portion by ninety degrees.

6. The method of claim 3, wherein the first remaining portion is mounted on the second support hub with a circuit of the first remaining portion facing a wall of the second support stub.

7. The semiconductor wafer test sample of claim 3, wherein mounting the first remaining portion on a support stub comprises rotating the first remaining portion by ninety degrees.

8. A method for preparing a sample wafer for plan view transmission electron microscopy, the method comprising:

microcleaving a sample wafer from a semiconductor wafer with an automated diamond sawing tool, the step of microcleaving further comprising, marking a selected location on the sample wafer with a diamond scribe, and cleaving the sample wafer at the marked location with the diamond sawing tool;

cutting the sample wafer with the automated diamond sawing tool to expose a cross sectional view surface of a first remaining portion of the sample wafer;

mounting the first remaining portion in an orientation for plan view imaging; and cutting the first remaining portion with the automated diamond sawing tool to expose a plan view surface of a second remaining portion of the sample wafer.

9. The method of claim 8, wherein cutting the sample wafer comprises:

mounting the sample wafer on a first support stub;

making a first cut in the sample wafer using a first saw blade, wherein the first cut does not cut through the sample wafer; and making a second cut in the sample wafer using a second saw blade, wherein the second cut cuts through the sample wafer and the first support stub.

10. The method of claim 9, wherein:

mounting the first remaining portion comprises:

removing the first remaining portion from the first support stub; and mounting the first remaining portion on a second support stub; and cutting the first remaining portion comprises:

making a first cut in the first remaining portion using a first saw blade, wherein the first cut does not cut through the first remaining portion; and making a second cut in the first remaining portion using a second saw blade, wherein the second cut cuts through the first remaining portion and the second support stub.

11. The method of claim 10, further comprising:

clamping a focused ion beam (FIB) clamp to a stub holder fixture that supports the second support stub; and cutting the second remaining portion of the sample wafer from the second support stub with the automated diamond sawing tool.

12. The method of claim 10, wherein mounting the first remaining portion on a second support stub comprises:

mounting a spacer to the second support stub; and mounting the first remaining portion to the spacer.

13. The method of claim 10, wherein mounting the first remaining portion on a second support stub comprises rotating the first remaining portion by ninety degrees.

14. The method of claim 10, wherein the first remaining portion is mounted on the second support hub with a circuit of the first remaining portion facing a wall of the second support stub.

15. A semiconductor wafer test sample prepared for plan view transmission electron microscopy, the test sample manufactured by:

microcleaving a sample wafer from a semiconductor wafer;

cutting the sample wafer to expose a cross sectional view surface of a first remaining portion of the sample wafer;

mounting the first remaining portion in an orientation for plan view imaging on a support stub;

cutting the first remaining portion and the support stub to expose a plan view surface of a second remaining portion of the sample wafer;

clamping a focused ion beam (FIB) clamp to a stub holder fixture that supports the support stub; and cutting the test sample from the support stub, wherein the test sample comprises a portion of the second remaining portion of the sample wafer and a portion of the support stub.

16. The semiconductor wafer test sample of claim 15, wherein mounting the first remaining portion on a support stub comprises:

mounting a spacer to the support stub; and mounting the first remaining portion to the spacer, and wherein the test sample further comprises a portion of the spacer.

17. The semiconductor wafer test sample of claim 15, wherein the first remaining portion is mounted on the support hub with a circuit of the first remaining portion facing a wall of the second support stub.

18. The semiconductor wafer test sample of claim 17, wherein the portion of the support stub comprises an imaging window.

* * * * *